United States Patent
Ladjevardi et al.

(10) Patent No.: US 7,214,531 B2
(45) Date of Patent: May 8, 2007

(54) PRESSURE TRANSDUCED CHEMICAL ASSAY AND METHOD

(75) Inventors: Mahmoud Ladjevardi, La Jolla, CA (US); Theodore Sand, Poway, CA (US)

(73) Assignee: Disan, Inc., San Diego, CA (US)

( * ) Notice: Subject to any disclaimer, the term of this patent is extended or adjusted under 35 U.S.C. 154(b) by 531 days.

(21) Appl. No.: 10/479,782

(22) PCT Filed: Apr. 15, 2002

(86) PCT No.: PCT/US02/12052

§ 371 (c)(1), (2), (4) Date: Feb. 9, 2004

(87) PCT Pub. No.: WO02/099430

PCT Pub. Date: Dec. 12, 2002

(65) Prior Publication Data

US 2004/0121418 A1    Jun. 24, 2004

(51) Int. Cl.
*G01N 33/543* (2006.01)
*G01N 33/558* (2006.01)

(52) U.S. Cl. .............. 435/287.2; 310/311; 310/313 R; 422/56; 422/57; 422/58; 435/6; 435/7.22; 435/7.32; 435/7.9; 435/7.92; 435/287.7; 435/287.9; 435/805; 435/810; 435/970; 436/514; 436/518; 436/530; 436/817

(58) Field of Classification Search ...................... None
See application file for complete search history.

(56) References Cited

U.S. PATENT DOCUMENTS 6,200,532 B1 *  3/2001  Wu et al. ..................... 422/73

* cited by examiner

*Primary Examiner*—Christopher L. Chin
(74) *Attorney, Agent, or Firm*—Fish & Associates, PC

(57) ABSTRACT

An assay system has a chamber that receives a test strip onto which a sample comprising an analyte has been placed. The chamber is in gaseous communication with a piezoelectric material that generates an electrical signal in response to a pressure change in the chamber that is caused by a reaction between the analyte and a reagent.

20 Claims, 3 Drawing Sheets

PRESSURE TRANSDUCED CHEMICAL ASSAY AND METHOD

This invention was made with Government support under Contract No. 68D60024 awarded by the US EPA and Contract No. R43 AI 43806-01 awarded by the NIAID. The Government has certain rights in the invention.

This application claims the benefit of U.S. provisional application No. 60/294861 incorporated herein by reference in its entirety.

FIELD OF THE INVENTION

The field of the invention is test systems for analytes.

BACKGROUND

Analysis of an analyte in a sample generally includes detection of the analyte. Detection may be classified as either direct or indirect. Direct detection typically includes observations that are readily apparent without any further chemical reaction. Indirect detection, on the other hand, often requires a chemical reaction before becoming readily apparent.

Indirect detection may include reactions that cause changes in mass. Devices that detect changes in mass, however, are often not amenable to certain types of samples. Another indirect detection involves events measured using labels that are radioisotopes. Such techniques, however, raise safety concerns.

Indirect detection may also include reactions that cause a change in color, fluorescence, and luminescence. Such changes, however, may be so slight that they are not readily detectable by the human eye. Slight changes in color of many known systems may be due to relatively small concentrations of analytes present in the samples. In addition, color changes and other photometric characteristics may be spread over too large an area to be very useful. Although devices and chemical reactions may be used to amplify signals, noise is often amplified as well.

Problems with detection are addressed by U.S. Pat. No. 5,518,895 issued to Thorpe et al. (May 1996). The '895 patent is directed toward a device and method that detects microorganisms in blood and other body fluids by measuring pressure changes within a sealable container. By measuring pressure changes, the accuracy of the analysis may be increased. Accuracy, however, may be negatively impacted by cleanliness and sterility of the container. Another problem may involve loss of gas caused by not sealing the container quickly enough after adding the reactant that causes the gas to be evolved.

U.S. Pat. No. 6,287,851 issued to Delwiche et al. (September 2001) teaches a sensor comprising a chamber having an inlet adapted to admit a liquid sample which gets pumped into a reaction cell using a pump. Problems exist in this system generally because it requires that a liquid sample enter the reaction cell. First, a liquid sample may not always be available. Second a sufficient volume of liquid may not be available to enable pumping to occur. Third, the existence of a pump and porous membrane to separate the liquid portion from the gaseous portion adds complexity to the sensor design.

Thus, there is a need for less complicated detection devices and methods, especially for low concentration analytes.

SUMMARY OF THE INVENTION

The present invention is directed toward analyzing an analyte contained on a collection strip. The analyte generally reacts with a reagent in a chamber. The reaction evolves a gas. A piezoelectric crystal, polymer or other material that produces an electrical signal in response to pressure changes caused by the gas is in gaseous communication with the chamber and the reaction.

There are some apparent disadvantages to using a collection strip. One disadvantage is that the analyte and/or reagent may bind to the strip and thereby distort the analysis. Another disadvantage is that capillary action may distort the analysis because the analyte on the strip may be impeded from wicking across the strip to the area where the reagent exists. Certain analytes may not reach the reagent at all.

The apparent disadvantages of using a collection strip are outweighed by less apparent advantages that result from the use of a collection strip in the inventive assay.

Various objects, features, aspects, and advantages of the present invention will become more apparent from the following detailed description of preferred embodiments of the invention, along with the accompanying drawings in which like numerals represent like components.

DETAILED DESCRIPTION

Figure 1:
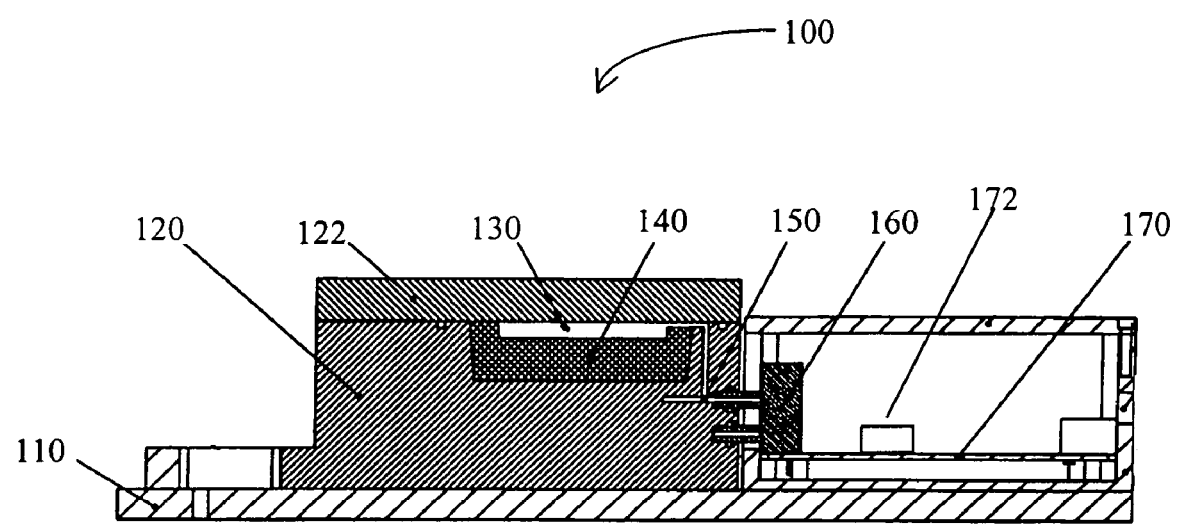
FIG. 1 is a schematic vertical cross section of a further exemplary assay system.

In FIG. 1, an assay system 100 generally comprises a base 110 and a housing 120, which forms together with lid 122, a chamber 130. Disposed within the chamber 130 is a strip holder 140 that receives a strip (not shown). Chamber 130 is in gaseous communication with the piezoelectric crystal 160 via gas conduit 150. The piezoelectric crystal 160 produces an electric signal that is processed in a circuitry (not shown) comprising a microprocessor 172 on the circuit board 170.

A test strip generally receives a sample comprising an analyte. As used herein, the term "analyte" refers to the at least one substance of which the presence or concentration is be determined. Therefore, contemplated analytes include single molecules, homo- and heterodimers, -trimers and -multimers, molecular assemblies (e.g., K-ATPase, microtubuli, etc.), molecular superstructures (e.g., biological membranes), and various organisms. Particularly preferred analytes include peptides of various molecular weights, nucleic acids (e.g., RNA, DNA, PNA, etc.), carbohydrates, hormones, pharmaceutical agents, lipids, bacteria, viruses, viroids, mammalian cells, parasites, chelated metal ions, or haptenic organic molecules.

It should be especially appreciated that the definition of analyte particularly includes complexes of the aforementioned substances and structures with a first compound, wherein the complex formation may be due to a covalent bond, a non-covalent bond (e.g., electrostatic, ionic, hydrophobic interaction, etc.), or any reasonable combination thereof. Particularly contemplated first compounds include various peptides, antibodies or their fragments, nucleic acids, enzyme, and metal ion chelators. Furthermore, it should be appreciated that contemplated first compounds may further include an enzyme that produces a gas when the enzyme reacts with the reagent. There are numerous methods of coupling an enzyme to a substrate, and all known methods are contemplated suitable for use in conjunction with the teachings herein.

It is generally contemplated that all enzymes that catalyze a reaction that produces a gaseous product are suitable, however, especially preferred enzymes include peroxidases, ureases, carbonic anhydrases and catalases from various sources. Further contemplated enzymes include decarboxylases (and particularly amino acid decarboxylases, oxalate DC, pyruvate DC, etc.), various dehydrogenases (pyruvate DH, isocitrate DH), and oxidases. Moreover, it should be recognized that more than one enzyme may be employed in the generation of a gas. For example, an enzyme coupled to the first compound may produce a first product, which is then substrate for one or more subsequent enzymatic and/or non-enzymatic reactions in which a gas is formed.

A chamber 130 receives a test strip, and the chamber is preferably sealed during the reaction such that the electric signal is sufficient to provide a qualitative assessment of the analyte (e.g., partially sealed). On the other hand, the chamber may be sealed during the reaction such that the electric signal is sufficient to provide a quantitative assessment of the analyte (e.g., hermetically sealed).

With respect to the chamber volume, it is contemplated that various volumes are suitable. However, it is generally preferred that the volume of the chamber relative to the sample allows a relatively rapid increase in pressure where the chamber is at least partially sealed. Consequently, it is preferred that the chamber volume is no greater than 5 times, and more preferably no greater than 3 times the volume of the sample that is applied to the test strip. It should be appreciated that the volume of the chamber relative to the sample is not meant to be a limitation, and as such the chamber volume may be 20, 50, or even 100 times or more than that of the sample.

A piezoelectric crystal 160, or other suitable material, is in gaseous communication with the chamber 130. The piezoelectric crystal 160 generates an electrical signal in response to a pressure change in the chamber caused by a reaction between the analyte and a reagent.

The term "reagent" as used herein refers to any substance or substrate that in a chemical reaction (preferably as substrate or cosubstrate of contemplated enzymes) will produce a gaseous compound. The term "gaseous compound" as used herein includes all compounds that have in their isolated form at atmospheric pressure a boiling point of lower than 25° C. Depending on the enzyme, contemplated substrates may vary considerably. However, especially preferred substrates include $H_2O_2$, urea, $HCO_3$, various amino acids, glucose, ethanol, salicylate, etc.

A microprocessor 172 is preferably located on a circuit board 170. A microprocessor may be any appropriate microprocessor (i.e., Intel Pentium 4, AMD Athlon, and so on). Depending on the particular configuration and point of use, contemplated configurations may include a microprocessor that transforms the electrical signal from the piezoelectric material into a user readable output, wherein the microprocessor may or may not be at least partially enclosed in the chamber.

In a preferred method of performing an assay, a sample is mixed with a solution comprising an antibody that binds the analyte with relatively high affinity (i.e., $K_D < 10^6 M^-$) to form a complex, wherein the antibody is further coupled to catalase. The resulting mix is applied to the sample receiving area of the test strip and moves (predominantly via capillary action) towards the wick on the opposite end of the test strip. The screening area on the test strip comprises immobilized analyte in a concentration effective to remove substantially all of the antibody that did not bind to the analyte in the sample (or excess antibody). As the mix passes the screening area, only complexes between the antibody and the analyte will pass towards the capture zone, while free antibodies (antibody without analyte) will be substantially retained in the screening area. The capture zone on the strip comprises immobilized antibodies that bind the complexes with relatively high affinity. Thus, the amount of bound complexes (bearing a gas producing enzyme) in the capture zone is substantially identical with the amount of analyte. A substrate solution is then applied to the capture zone and at least the capture zone is placed in the chamber to detect evolving gas from the reaction between the reagent and the analyte.

Figure 2:
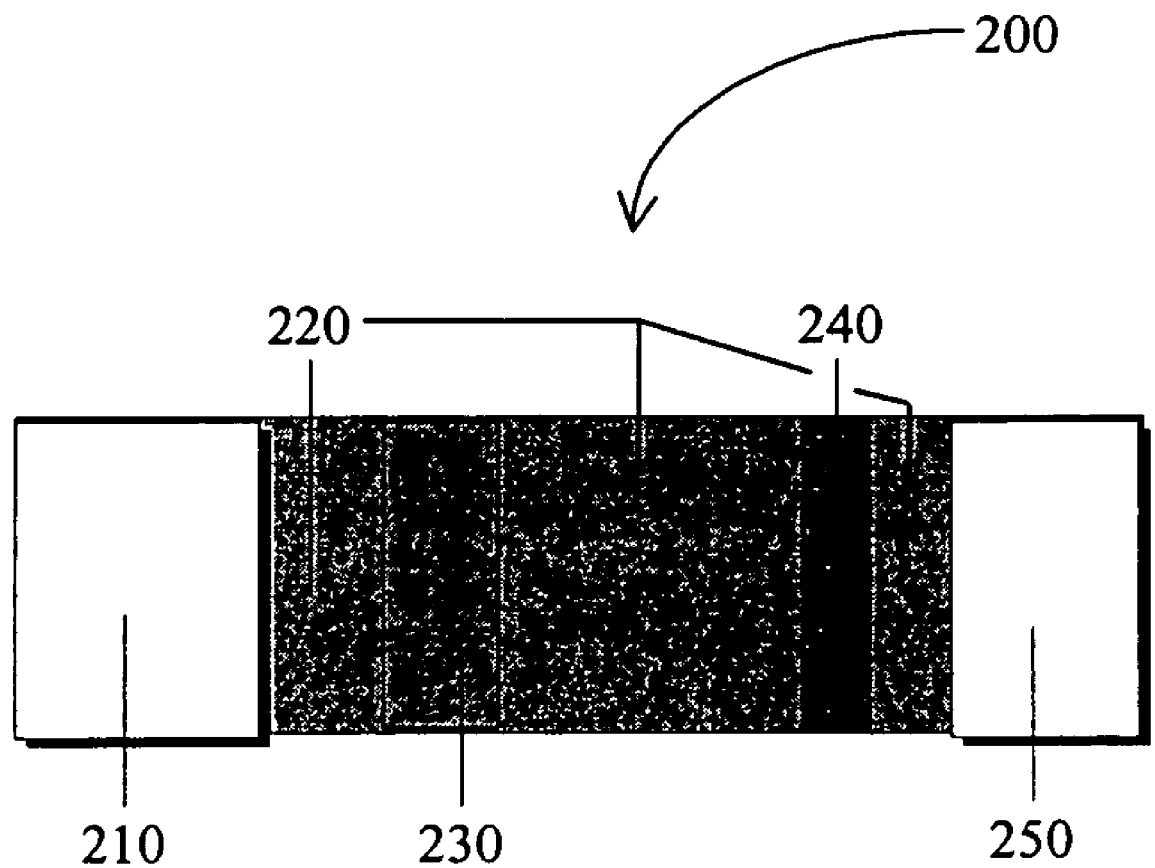
FIG. 2 is a schematic view of an exemplary test strip.

In a preferred aspect of the inventive subject matter, the test strip has a configuration as depicted in FIG. 2. Here, the test strip 200 is manufactured on a base of Mylar™ (not shown) onto which (from left to right) a sample receiving zone 210 is juxtaposed to an area of nitrocellulose 220, which is adjacent to a screening zone 230. The screening zone 230 is followed by another nitrocellulose area 220 juxtaposed to a capture zone 240, a nitrocellulose area 220, and a wick 250. Thus, a sample applied to the sample receiving zone 210 will travel through the nitrocellulose area via the screening zone and capture zone to the wick by virtue of capillary action.

Figure 3:
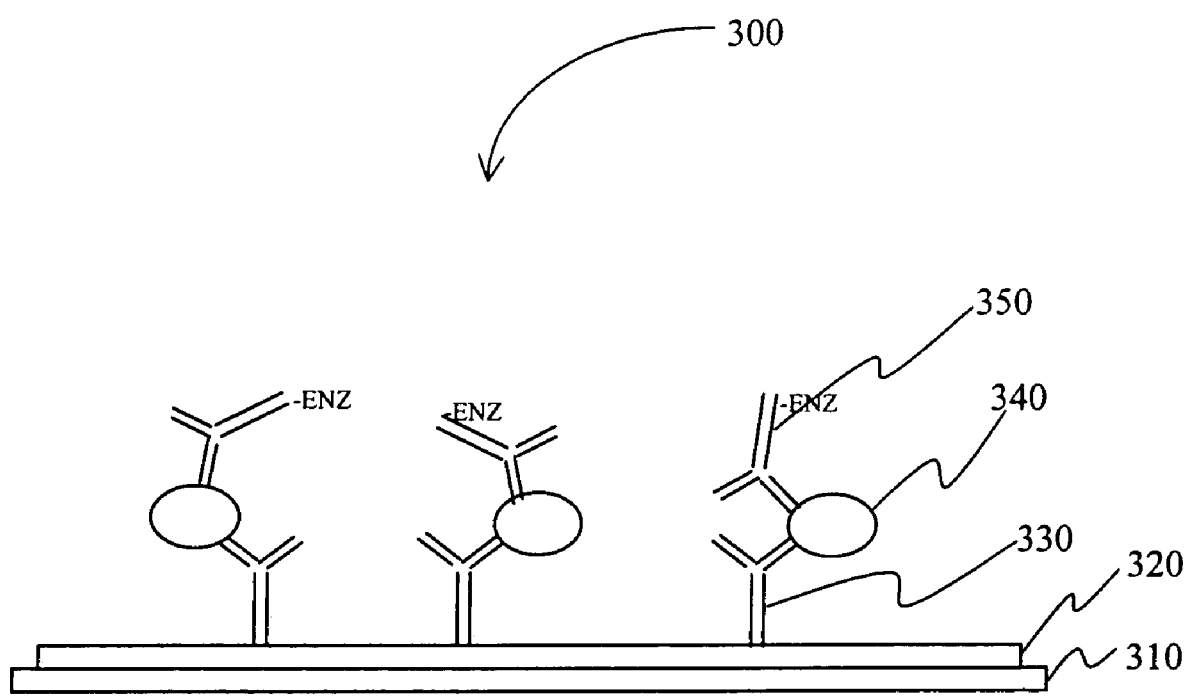
FIG. 3 is a schematic of an exemplary "sandwich" configuration in an exemplary assay system.

In alternative aspects, a "sandwich format" (e.g., a carrier material with capture antibodies binds the antigen, which binds in turn a detector antibody) may be employed for detection of a target antigen. For example, particularly contemplated carriers include nitrocellulose membranes (with optional backing such as a sticky Mylar™ membrane) or other membranes to which antibodies can be coupled. It is further preferred that suitable membranes are blocked after application of the capture reagent to minimize non-specific binding of subsequent reagents and/or sample. The sample containing the antigen can then be applied to the capture zone (e.g., via capillary action or pipetting) and incubated for an appropriate amount of time. A washing step will remove unbound antigen, and subsequently detector reagent can be added over the capture zone comprising the antigen. After incubation for an appropriate amount of time, the carrier is washed and the capture zone placed in a sealable test chamber. Substrate solution is added, and the capture zone is coupled to a pressure sensor in gaseous communication to record evolution of gas (signal being measured in mV). Thus, an exemplary sandwich could have a configuration as depicted in FIG. 3. Here, the sandwich 300 comprises a backing 310 onto which a nitrocellulose membrane 320 is attached. Bound to the membrane 320 is a plurality of capture antibodies 330 that bind the analyte 340. The analyte is detected with a detection antibody 350, which is coupled to an enzyme.

EXAMPLES

A lateral-flow assay was constructed based on commercially available reagents and enzyme conjugates. The assay was developed with a screening zone and a capture zone, in order to generate signals that were directly proportional to the concentration of the test substrate atrazine. This assay was evaluated in a pressure sensing test bed for the ability to respond to atrazine in spiked buffer samples. The test system produced signal differentials of approximately 3.5-fold for samples with 1 ppm atrazine compared to negative samples.

Biological/Immunochemical Reagents

The antibody against atrazine was obtained from Biostride, Inc. (Palo Alto, Calif.). Atrazine-BSA also was obtained from Biostride. The Goat anti-Rabbit IgG was obtained from Jackson ImunoResearch Laboratories (West Grove, Pa.). All other chemicals were obtained from Sigma Chemical, Co. (St. Louis, Mo.), Aldrich (St. Louis, Mo.), Pierce Chemical Co. (Rockville, Ill.) or Pharmacia (Piscataway, N.J.).

Pressure Sensing Components

The multimeter and various electrical components were obtained from Radio Shack. The pressure chamber, the assay strip holder and the mounted pressure sensor were fabricated by J M Speciality Parts (San Diego, Calif.). The piezofilm was obtained from AMP, Inc (Folsom, Calif.). The pressure sensors were obtained from SenSym, Inc. (Sunnyvale, Calif.).

Enzymes and Antibodies

Urease, carbonic anhydrase, catalase, peroxidase, and their respective substrates were purchased from Sigma. The enzymes were purified and biotinylated following standard protocols known in the art. Similarly, anti-atrazine antibodies were purchased from Sigma and conjugated with streptavidin following standard protocols known in the art.

Conjugate Formation

Streptavidin-containing antibodies and biotin-containing enzymes ware conjugated by mixing (with excess of biotinylated enzyme). The mixture is incubated at room temperature for 2 hr and then overnight at 4° C. with gentle shaking. After incubation, the mixture is run on a Sepharose S300 column and the leading edge of the first peak is collected. The collected fractions were evaluated for the presence of antibody reactive with atrazine in an ELISA under standard conditions. The results from ELISA analysis indicated that antibody and enzyme had formed conjugates, since antibody activity was found in the pools made from the leading edge of the elution profiles of both urease and catalase.

Test Strip Components and Preparation

Nitrocellulose is lightly marked with pencil to indicate the location of the screening and capture zones. The screening zone material is diluted in 10 mM Tris (pH 8.5) to give a concentration of 1 mg/ml. Approximately 10 μl of the solution is spotted in the appropriate zone. The antibody used for the capture zone is diluted in 10 mM Tris (pH 8.5) to give a concentration of 1 mg/ml. Approximately 8 μl of the solution is spotted in the appropriate zone. After drying at 45° C. for 15 min, the nitrocellulose is placed in excess 10 mM Tris buffer with 10 mg/ml BSA. The nitrocellulose is blocked for 2 hrs at room temperature, after which it is blotted with paper towels and placed at 45° C. for 1 hr. The sample pad material is blocked and dried following known procedures. A strip of sticky mylar (2 mil thickness) is placed on a flat surface. A blocked strip of nitrocellulose is placed on the mylar, leaving some sticky surface at both ends of the strip. The sample pad is placed to the left of the screening zone and the absorbent pad is placed at the other end. The materials are pressed gently into the mylar strip. The completed strips are stored in a desiccator at room temperature.

Assay Procedure

A strip is removed from the desiccator and placed on a flat surface. The antibody-catalase conjugate (at the appropriate dilution made in 10 mM Tris [pH 8.5] with 1 mg/ml BSA) is added to the strip to the left of the screening zone. Approximately 250 μl of the Tris/BSA solution is added to the sample pad. The liquid is allowed to wick to the sample absorbent pad for 20–30 min, depending on the strip's wicking rate. The capture zone and the screening zone are cut from the strip and tested in the pressure sensing test bed. Atrazine was spiked into the antibody-catalase conjugate at the appropriate level and incubated at room temperature for a minimum of 2 hrs before testing.

The test bed is turned on and allowed to stabilize for 10 min prior to use. The test chamber is cleaned with $dH_2O$ and 70% Isopropyl alcohol. 300 μl of the enzyme substrate solution is added to the chamber. The chamber is sealed and the tubing is connected to the sensor test bed. A timer is started and the initial pressure reading (in mV) is recorded. The chamber is rotated gently for 15 sec, and is rotated for 30 sec at 1 min and again at 3 min. A reading is taken at 5 min.

Results

The average (±1.0 standard deviation) change in pressure was determined in millivolts produced during a 5 min testing period. The obtained data (and further data, not shown) confirm that contemplated pressure-based assays are responsive to concentrations of the analyste in a sample with a sensitivity of lower limit of detection in the order of 10 ppb at a signal differential of approximately 3.5-fold.

| ATRAZINE LEVEL (ppm) | CAPTURE ZONE (mV)* |
| --- | --- |
| 0 | 3.5 ± 1.0 (n = 5) |
| 0.01 | 3.9 ± 0.3 (n = 3) |
| 0.1 | 6.5 ± 1.3 (n = 3) |
| 1.0 | 11.7 ± 1.1 (n = 3) |

Alternative Assay Procedure (Sandwich Format)

In an alternate immunoassay strip format, nitrocellulose was spotted with capture reagent and then blocked as described above. The blocked strip was mounted on a sticky mylar backing, but the sample and wick materials were not attached. Antigen was allowed to migrate through the capture zone, wherein the antigen was applied to the end nearest the capture zone. After a brief rinse with deionized water, the strip was placed flat and detector reagent was added over the capture zone. After 15–30 minute incubation, the strip was washed with deionized water. The capture zone was cut from the strip and placed in a sealable test chamber. Substrate solution was added, the chamber was sealed and the system connected to the pressure sensor to record evolution of gas (signal being measured in mV). The results obtained for this alternative biosensor suggest the ability to detect levels of extracted antigen associated with 10–100 oocysts per mL.

Thus, specific embodiments and applications of pressure transduced chemical assays and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An assay system comprising:
   a test strip that receives a sample comprising an analyte;
   a chamber that receives the test strip; and
   a piezoelectric material in gaseous communication with a lumen of the chamber such that the material generates an electrical signal in response to a pressure change in the chamber caused by a reaction between the analyte and a reagent.

2. The assay system of claim 1 wherein the chamber is at least partially sealed during the reaction between the analyte and the reagent.

3. The assay system of claim 2 wherein the chamber is sealed during the reaction such that the electric signal is sufficient to provide a qualitative assessment of the: analyte.

4. The assay system of claim 2 wherein the chamber is sealed during the reaction such that the electric signal is sufficient to provide a quantitative assessment of the analyte.

5. The assay system of claim 1 wherein the analyte forms a complex with a first compound, and wherein the test strip further comprises a second compound that binds the complex.

6. The assay system of claim 5 wherein the first compound further comprises an enzyme, and wherein the reagent reacts with the enzyme to produce a gas.

7. The assay system of claim 6 wherein the enzyme is selected from the group consisting of peroxidase, urease, carbonic anhydrase and catalase.

8. The assay system of claim 5 wherein the second compound comprises an antibody.

9. The assay system of claim 1 wherein the analyte is selected from a group consisting of a peptide, a nucleic acid, a carbohydrate, a hormone, a pharmaceutical agent, a lipid, a bacterium, a virus, a viroid, a mammalian cell, a parasite, a chelated metal ion, and a haptenic organic molecule.

10. The assay system of claim 1 wherein the analyte is selected from a Cryptosporidium parvum oocyst, a polypeptide from Cryptosporidium parvum, and a nucleic acid from Cryptosporidium parvum.

11. The assay system of claim 1 wherein the first compound is selected from the group consisting of a peptide, an antibody, a nucleic acid, an enzyme, and a metal ion chelator.

12. The assay system of claim 1 further comprising a microprocessor that transforms the electrical signal into a user readable output.

13. The assay system of claim 12 wherein the microprocessor is at least partially enclosed in the chamber.

14. The assay system of claim 1 wherein the test strip comprises a sample application zone, a screening zone, a capture zone, and a wick.

15. The assay system of claim 14 wherein the screening zone comprises immobilized analyte.

16. The assay system of claim 14 wherein the capture zone comprises an immobilized second compound.

17. The assay system of claim 1 wherein the analyte is an antigen from Cryptosporidium parvum and forms a complex with an antibody that is labeled with catalase, and wherein the complex is bound by an anti-antibody that is immobilized in a capture zone of the test strip, and wherein the pressure change in the chamber is produced by a reaction of the catalase with a substrate.

18. The assay system of claim 1 wherein the sample is applied to a capture zone on the test strip, and wherein the capture zone comprises an antibody that binds the analyte.

19. The assay system of claim 18 wherein the analyte bound to the antibody is detected by a detector molecule.

20. The assay system of claim 19 wherein the detector molecule comprises an antibody that is conjugated with an enzyme.

* * * * *